(12) United States Patent
Esler

(10) Patent No.: US 6,795,735 B2
(45) Date of Patent: Sep. 21, 2004

(54) METHOD AND APPARATUS FOR RECORDING FAULT HISTORY INFORMATION

(75) Inventor: James A. Esler, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 445 days.

(21) Appl. No.: 10/052,887

(22) Filed: Jan. 17, 2002

(65) Prior Publication Data

US 2003/0135244 A1 Jul. 17, 2003

(51) Int. Cl.[7] .............................................. A61N 1/37
(52) U.S. Cl. .................................................. 607/27
(58) Field of Search ................................. 607/1–156

(56) References Cited

U.S. PATENT DOCUMENTS 4,625,730 A * 12/1986 Fountain et al. ............... 607/4

* cited by examiner

Primary Examiner—Scott M. Getzow
(74) Attorney, Agent, or Firm—Thomas J. Nikolai; Nikolai & Mersereau, P.A.

(57) ABSTRACT

An implantable medical tissue stimulating device is designed to capture fault history relating to error events in a manner that allows subsequent analysis of operational performance prior to, during and subsequent to the occurrence of a detected error. Physiologic and operational data are fed through a buffer capable of temporarily storing such data over a predetermined interval. When a fault condition is detected, a trigger signal is generated a predetermined time following the occurrence of the fault condition and, upon generation of the trigger signal, the contents of the buffer are stored away in a RAM memory for subsequent read-out.

8 Claims, 2 Drawing Sheets

METHOD AND APPARATUS FOR RECORDING FAULT HISTORY INFORMATION

BACKGROUND OF THE INVENTION

I. Field of the Invention

This invention relates generally to implantable electronic tissue stimulating systems, and more particularly to a method and apparatus for recording for subsequent read-out physiologic and operational data occurring a predetermined time prior to, during and after detection of a fault condition whereby diagnosis and evaluation of a stimulating system malfunction is enhanced.

II. Discussion of the Prior Art

While the present invention may find application in a variety of implantable medical tissue stimulating systems, the present invention will be described in the environment of cardiac rhythm management devices, including bradycardia and tachycardia pacemakers and automatic implantable defibrillators. However, limitation of the invention to cardiac rhythm management devices should not be inferred in that it may also be used in neural stimulating systems as well.

Pacemakers have advanced from non-programmable, single-chamber, asynchronous devices (VOO) to dual-chamber, multi-mode systems with extensive programmability. For example, state-of-the-art pacemakers include the ability to automatically adjust the pacing rate on the basis of signals that are independent of the intrinsic heart rhythm (DDDR). The analysis/trouble shooting of a pacing system was comparatively easy during the early days of pacing, whereas the challenge in evaluating the modern pacemaker has increased to a degree that is concordant with the sophistication of the current devices.

To facilitate these evaluations, manufacturers have incorporated a multitude of diagnostic tools in their cardiac rhythm management products. The various diagnostic tools commonly complement one another, either eliminating the need for ancillary testing or providing an indication of direction for additional testing. Occasionally, a given feature provides absolute unique information that is not readily available by any other technique. These tools, which are integral to the implanted device, can be accessed by an external programmer, via a telemetry link. To take advantage of these diagnostic features and to determine the appropriate function of a stimulating system, the clinician must have an in-depth knowledge of the system components, including not only the pulse generator employed, but also the medical leads used to couple the pulse generator to the target tissue, programmed parameters, sensors, as well as the patient's physiology.

State-of-the-art implantable medical stimulators commonly incorporate a telemetry link allowing transmission of information or data between the implanted device and an external programmer/monitor. Such a telemetry link provides the ability to non-invasively change the functional parameters of the implanted device by coded commands transmitted to it from the external programmer and the ability of the implanted device to, in turn, transmit operational and physiologic data back to the external programmer/monitor for analysis by trained medical personnel. Bi-directional telemetry allows the implanted unit to be interrogated about its program parameters when the patient is seen during follow-up or is evaluated for suspected pacing system malfunction. Without this feature, there would be no way to determine the current settings of a device for features other than rate and pulse width. It also makes the retrieval of detailed data collected by the pacemaker in its various event counters feasible.

The introduction of dual chamber pacing has significantly increased the level of complexity of the paced rhythm. The interaction between two or more channels of the pacing system with the spontaneous rhythms occurring in either the atria or ventricles added to the potential for confusion. The addition of rate-modulated pacing (i.e., allowing the pacemaker to respond also to one or more sensor signals that are invisible on a surface ECG) further contributes to the challenge of interpreting the paced ECG because these sensor signals are frequently invisible on the surface ECG.

Thus, in current, state-of-the-art cardiac rhythm management devices, interpretation of a paced rhythm requires knowledge of the basic timing intervals. A variety of refractory periods, including post-ventricular atrial refractory period (PVARP), post-ventricular atrial blanking period, ventricular refractory period, ventricular blanking period, and paced and sensed atrioventricular (AV) intervals, must also be considered. Certain of these intervals vary depending on the instantaneous rate. Hence, the clinician needs to be aware of a number of device-specific responses to protect the system from a variety of anticipated, but undesirable behaviors or clinical events. These include cross-talk, a premature ventricular beat initiating a pacemaker-mediated tachycardia, mode switching, and multiblock upper rate behavior.

To facilitate interpretation of the paced rhythm, increasing numbers of pacing systems incorporate the ability to transmit information regarding real-time pacing system behavior to the external programmer on a virtually continual basis and to display this information on a screen or other recording system. Both paced and sensed events are communicated to the programmer. Displayed as a series of positive or negative marks, with or without alpha/numeric annotation, these are generally termed event markers. These event markers are generally superimposed above or below a simultaneously recorded surface ECG. The simultaneous ECG and markers allow the clinician to correlate the behavior of the pacemaker directly with the patient's rhythm to determine whether the system is functioning properly.

Most prior art implantable medical devices having event marker telemetry is limited to real-time recordings. The markers must be telemetered from the implanted device to the programmer while the rhythm is being actively monitored. Neither the pacemaker nor the programmer can retrospectively provide markers for previously recorded rhythms. If the implanted device is responding to events that are not visible on the surface ECG, the event marker simply confirms this fact, but does not identify the specific signal. An evaluation of sensed, but otherwise invisible events, requires electrogram (EGM) telemetry or an invasive procedure to record the signal from the implanted lead. More recently, implantable pacemakers have been introduced that have the capability of storing event markers with or without EGMs. These may be stored by the use of a patient trigger, such as the application of an external magnet proximate the site of the implanted device or a device triggered event.

As those skilled in the art appreciate, the recorded signal that enters the pacemaker's sense amplifier by way of the electrodes located within or on the heart is termed an intracardiac EGM. It is composed of a number of elements. The portion that is sensed by the pacemaker is termed the intrinsic deflection and reflects the rapid deflection that occurs when the wave of cardiac depolarization passes by the electrode. The intrinsic deflection can be characterized by both the amplitude and slew rate. The other portion of the cardiac depolarization, as reflected by the EGM, are termed the extrinsic deflection.

Real-time telemetry of event markers and EGM waveforms only allows the physician to analyze the behavior of the pacing system when the patient is in the physician's office or clinic while these diagnostics are being accessed with the programmer. This is impractical over a long period. Long-term monitoring of pacing system behavior requires either a Holter monitor, which is expensive and cumbersome, or event counter telemetry, depending on the degree of precision that is desired. Implantable medical devices, with microprocessor-based controllers and significant random access memory (RAM), can store selected EGMs as well as event markers when triggered by the patient or by a predefined set of circumstances. However, due to memory size constraints, it is impossible to continuously store EGM waveforms and event markers for later readout upon the patient visiting the physician's office or clinic.

Implantable medical devices incorporating microprocessor-based controllers that receive sensed depolarization signals and other information and then process the information in accordance with an operating system and applications program embedded in firmware provide control signals to a pulse generator for delivering stimulating impulses to target tissue at times dictated by the microprocessor-based controller. The hardware used in implementing the microprocessor-based controller and pulse generator which it controls incorporate error detection logic which, for example, will prevent operation of the pulse generator at too high a rate, even though directed to do so because of an error in the firmware or an error due to erroneous programming. Such an error will generally cause the hardware to report the error condition back to the firmware which then makes note of the error and the time that it occurred. The hardware may also include an audible alarm which will "beep" upon the occurrence of an error being detected, thereby informing the patient that he/she should come into the physician's facility to have the system checked out. At this point, the physician may choose to call the manufacturer's Technical Services Group for assistance in determining what may have produced the fault. However, with prior art systems, all that can be derived is that the event took place and at what particular time it did.

Accordingly, there is a need for a method of recording fault history information which would be useful to Technical Service personnel in determining what may have caused a particular fault in the operation of the implanted medical device. The present invention fulfills that need.

SUMMARY OF THE INVENTION

The present invention provides a method and an apparatus for capturing operational history of an implantable medical device at a time prior to, at, and after a detection of a fault condition for subsequent analysis to assess the cause of the fault condition. The method involves providing an implantable medical device having a microprocessor-based controller with a memory and a storage buffer. The storage buffer temporarily stores operational and physiologic data, e.g., event markers and EGM data over a defined time interval. When the occurrence of a fault condition is detected in the operation of the implantable medical device, a triggering signal is produced a predetermined time following the detection of the fault condition and this triggering signal is used to transfer the then contents of the storage buffer into the memory. For example, continuously arriving operational and physiologic data may be applied as an input to a FIFO buffer that is sized to contain such data spanning a ten second interval and the triggering signal may be produced, say, five seconds after the detection of the fault condition. Then, when the triggering signal causes the contents of the storage buffer to be transferred into and stored in an addressable location in the memory, a "snap shot" is effectively taken of what happened in the implanted medical device before, during and after the occurrence of the fault.

Using the telemetry capability of the system, this history information can later be read out from the RAM and supplied to the manufacturer's Technical Service personnel whose knowledge of the system will better aid them in determining the ultimate cause of the fault in question.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
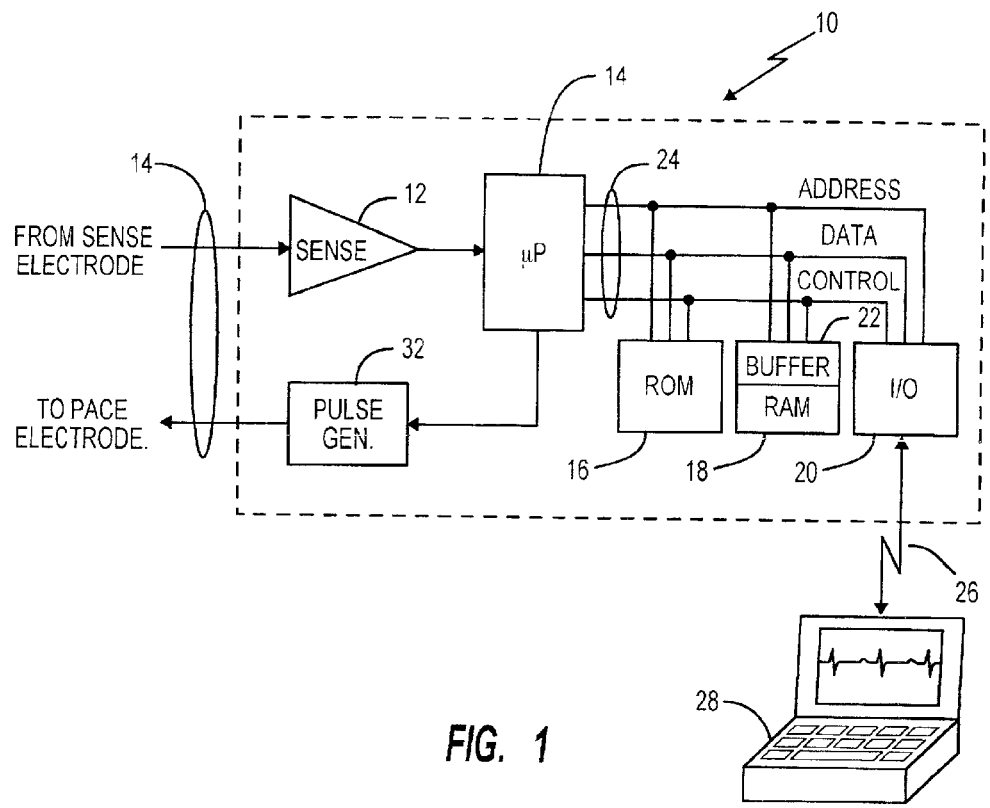
FIG. 1 is a block diagram of an implantable medical device in which the method of the present invention may be carried out.

Referring first to FIG. 1, there is schematically illustrated the hardware of a conventional implantable medical device indicated generally by numeral 10. For illustrative purposes only, the device 10 may comprise an implantable cardiac pacemaker of a type having a sense amplifier 12 coupled by a suitable medical lead 14 to a sensing electrode (not shown) located on or in a patient's heart. The sense amplifier operates in a conventional manner to amplify and signal process electrical depolarization signals picked up by the sense electrode and applies the signal processed signals to a data input terminal of a microprocessor-based controller 14.

Associated with the microprocessor-based controller 14 is a read-only memory (ROM) 16, a read/write random access memory (RAM) 18 and an input/output (IO) interface 20. The ROM 16 typically stores the operating system software for the microprocessor in the microprocessor-based controller 14 and because it is generally unalterable, it is commonly referred to as the system firmware. The RAM 18 also stores application-based programs as well as programmable parameters used in the execution of the software and firmware routines and, in accordance with the present invention, includes one or more memory registers configured as a FIFO buffer 22. Those skilled in the art will appreciate that the buffer 22 may be a section of the RAM 18 or it may comprise a module external to the RAM 18 but tied to the bus 24.

The I/O module 20 provides an interface for a telemetry link 26 coupling the implantable device 10 to an external programmer/monitor 28 to allow bi-directional communication therebetween.

The microprocessor-based controller is adapted to provide control signals over line 30 to a pulse generator 32 causing it to output stimulating pulses of a preprogrammed amplitude and duration at predetermined times to one or more stimulating electrodes also disposed on the medical lead 14.

Figure 2:
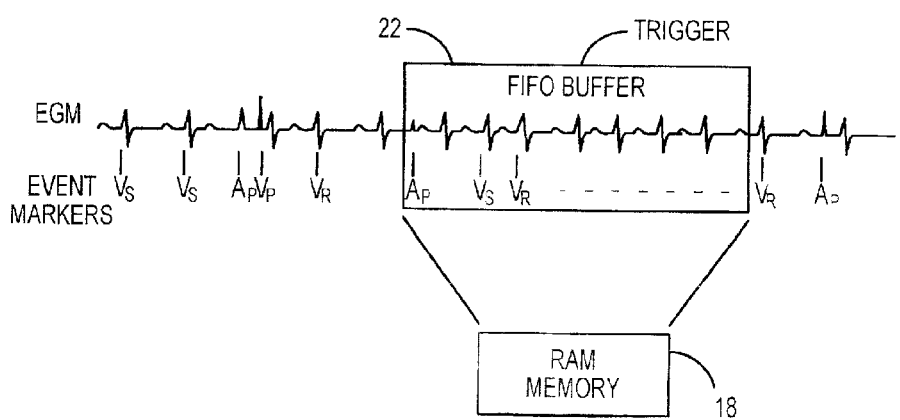
FIG. 2 is a block diagram of a FIFO buffer used in the system of FIG. 1 for continuously recording operational and physiologic data received by and developed in the hardware of FIG. 1.

Those skilled in the art will appreciate that the schematic representation illustrated in FIG. 1 has been significantly simplified and in actual practice would typically include both atrial and ventricular sensing and atrial and ventricular pacing. It might also typically include one or more physiologic sensors configured to adapt the pacing rate to a patient's level of physical activity so as to maintain a cardiac output commensurate with metabolic demand. Further, the microprocessor-based controller 14 may be programmed to operate in a known variety of modes. As has been indicated in the introductory portion of this specification, with this increased complexity comes an attendant difficulty in determining whether a software error, a hardware error or a combination of the two may have caused a malfunction. In accordance with the present invention, incoming electrogram signals from the sensing amplifier 12 are applied as inputs to the FIFO buffer 22 as illustrated schematically in FIG. 2. While in FIG. 2 the EGM signals are represented in an analog form, those signals would typically be applied to an AID converter (not shown) before being applied to the microprocessor-based controller 14 and the buffer 22 of the RAM memory 18.

Applied along with the EGM signals to the buffer 22 are event markers that are aligned time wise with excursions in the EGM waveform. Such event markers may include an indication of a ventricular sense ($V_S$), atrial pace ($A_P$), ventricular pace ($V_P$), ventricular refractory pace ($V_R$) and others.

The buffer 22 may be sized to store EGM and event markers occurring during a defined interval. For example, and without limitation, the FIFO buffer 22 may be sized to store a requisite number of bytes of data occurring during a 10 second interval. As new data enters the buffer 22, data more than 10 seconds old, in the example given, will be lost. However, in the event that the error detection circuitry implemented in the microprocessor-based controller 14 detects an error event, a trigger signal is generated a predetermined time, e.g., 5 seconds, following the detection of the error event. This trigger signal is used to cause the contents of the FIFO buffer 22 at the time that the trigger signal is generated to be stored at an addressable memory location within the RAM memory 18. Because of the delay introduced between the time of occurrence of the error event and the time at which the trigger signal is generated, the waveform sample and event markers being transferred into an addressable location in the RAM memory 18 will reflect data prior to, during and after the occurrence of the error.

Once the information transferred from the FIFO buffer has been captured in the RAM memory 18, it remains there for later retrieval by medical personnel via the telemetry link 26. This error history information will then aid the physician in determining just what caused the error in the first instance and, in this regard, the physician may avail himself/herself with the manufacturer's Technical Service personnel who may more familiar with the internal workings of the device.

Figure 3:
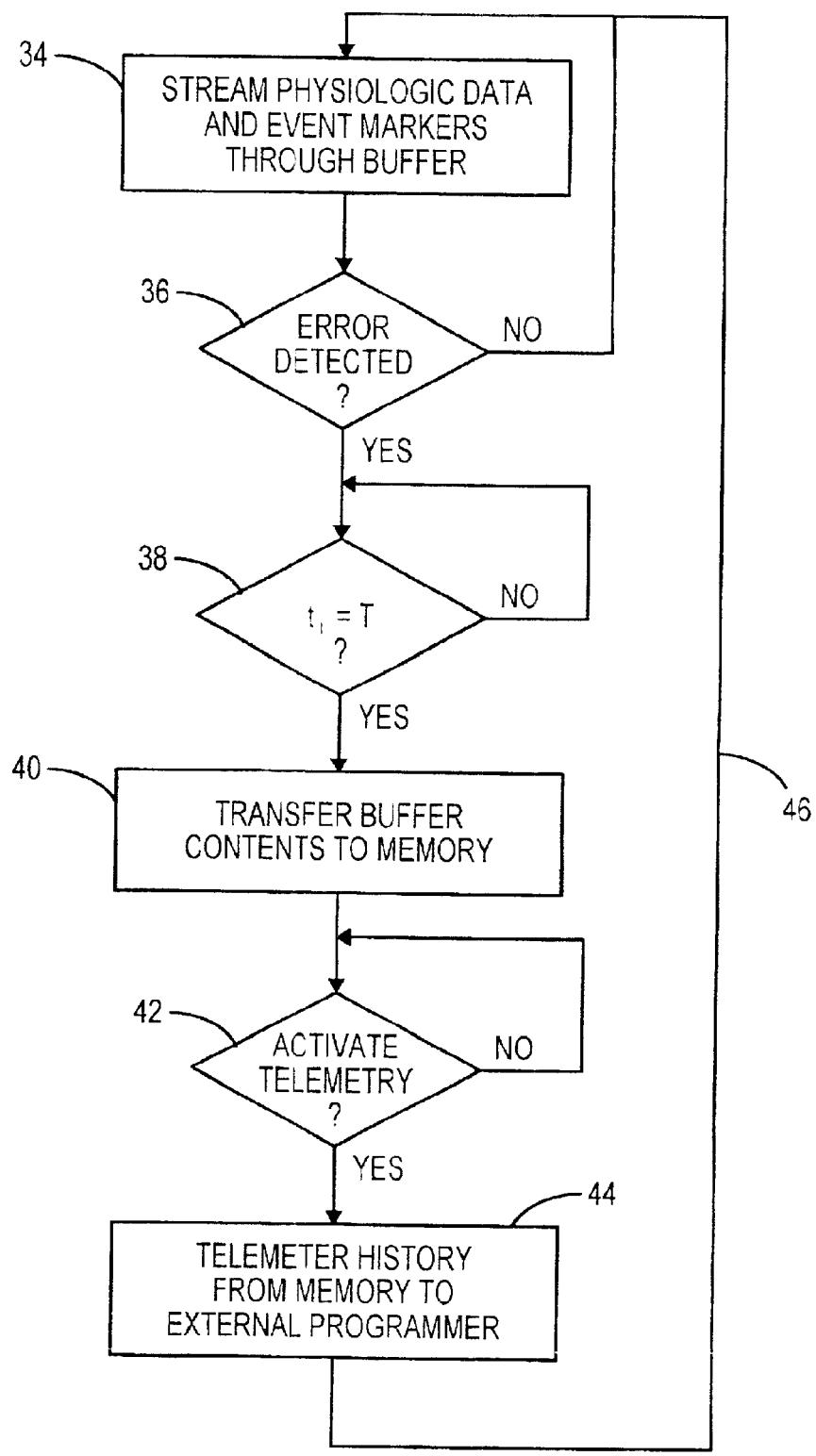
FIG. 3 is a flow diagram helpful in explaining the methodology comprising the present invention.

Referring next to FIG. 3, there is shown a high level flow diagram of the algorithm implemented in the implantable medical device for capturing fault history information. As is reflected in block 34, electrogram information passing through the sense amplifier 12 and event markers appended thereto by the microprocessor-based controller 14 are streamed through the buffer 22 on a continuous basis. Error detection circuitry in the hardware continually looks for error events such as, for example, memory corruption, long charging times for output capacitors in the pulse generator 32, watchdog interrupts, out-of-limit pacing rates, etc. Upon the detection of such an event as represented by decision block 36, a timer is initiated (block 38) and when a predetermined time, T, elapses, the contents of the buffer 22 are read into and stored in the RAM memory 18. See block 40. Because of the predetermined delay between the detection of the error and the transfer of the buffer contents to the memory, what becomes stored in the memory are EGM data and event markers relating thereto that extend from a time prior to the occurrence of the error, the error event itself and a time subsequent to the error occurrence.

The captured data remains in the memory of the implanted device until such time as the telemetry link 26 is activated (block 42). At this time, the history information from the memory is telemetered to the external programmer 28 for analysis and/or for further transfer to the device manufacturer's Technical Service representatives for analysis to determine the fault condition in the first instance. See block 44. It is, of course, to be understood that the algorithm of FIG. 3 may continue to run, allowing collection of data on a plurality of error events with the history information for each being stored in separate locations in the memory 18. This algorithm may be executed on a continuous basis as reflected by the loop 46.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A method of capturing operational history of an implantable medical device before, during and after detection of a fault condition for subsequent analysis to assess the cause of the fault condition, comprising:

(a) providing an implantable, medical device having a microprocessor-based controller with a memory and a storage buffer, the storage buffer temporarily storing operational and physiologic data over a defined time interval;

(b) detecting the occurrence of a fault condition in the operation of the implantable medical device and producing a triggering signal a predetermined time following the detection of the fault condition; and (c) storing the contents of the storage buffer in the memory upon the occurrence of the triggering signal.

2. The method of claim 1 wherein the trigger signal is produced at a time relative to the detection of the occurrence of the fault condition such that said data occurring prior to, during and after the fault condition are stored in the memory.

3. The method of either claim 1 or claim 2 and further including the step of:

(a) transmitting contents of the memory to an external monitor for analysis in determining a possible cause of the fault condition.

4. The method of claim 1 wherein the defined time interval is on the order of several seconds and said predetermined time is on the order of about one-half the said time interval.

5. The method as in any one of claims 1, 2 or 4 wherein the implantable medical device is a cardiac rhythm management device, the operational data comprise event markers and the physiologic data comprise cardiac electrogram signals.

6. In an implantable medical device, apparatus for capturing fault history information for subsequent analysis, comprising:

(a) a microprocessor-based controller;

(b) a sense amplifier coupled to receive cardiac electrogram signals and to deliver same to the microprocessor-based controller;

(c) a random access memory operatively coupled to the microprocessor-based controller;

(d) a FIFO buffer of a size capable of storing the sensed electrogram signals and event markers generated by the microprocessor-based controller over a defined time interval;

(e) means in the microprocessor-based controller for detecting fault conditions in the operation of the implantable medical device and producing a trigger signal a predetermined time following a detection of a fault condition;

(f) means for transferring the contents of the FIFO buffer to the random access memory upon the occurrence of the trigger signal; and (g) a telemetry link controlled by the microprocessor based controller for reading out information from the random access memory to an external monitor.

7. The apparatus as in claim 6 wherein the FIFO buffer is of a size to contain said electrogram signals and event markers occurring during a time interval of several seconds.

8. The apparatus of claim 7 wherein the trigger signal is produced at a time following detection of a fault condition that is about one-half of said time interval.

* * * * *